United States Patent
Johnson et al.

(10) Patent No.: US 9,861,978 B2
(45) Date of Patent: Jan. 9, 2018

(54) MECHANICALLY ACTUATED VACUUM CONTROLLED FLUID COLLECTION

(71) Applicant: Boston Microfluidics, Cambridge, MA (US)

(72) Inventors: Brandon T. Johnson, Sommerville, MA (US); Kate E. Christian, Cambridge, MA (US); Glenn H. Verner, Powell, OH (US)

(73) Assignee: BOSTON MICROFLUIDICS, INC., Boston, MA (US)

( * ) Notice: Subject to any disclaimer, the term of this patent is extended or adjusted under 35 U.S.C. 154(b) by 0 days.

(21) Appl. No.: 14/098,280

(22) Filed: Dec. 5, 2013

(65) Prior Publication Data
US 2014/0341787 A1    Nov. 20, 2014

Related U.S. Application Data

(60) Provisional application No. 61/733,516, filed on Dec. 5, 2012.

(51) Int. Cl.
*B01L 3/02* (2006.01)
*G01N 1/14* (2006.01)
(Continued)

(52) U.S. Cl.
CPC ............ *B01L 3/502* (2013.01); *A61B 10/007* (2013.01); *B01L 2200/16* (2013.01);
(Continued)

(58) Field of Classification Search
CPC ............... B01L 3/502; B01L 2200/16; B01L 2300/0832; B01L 2300/0864; B01L 2400/0478; A61B 10/007
See application file for complete search history.

(56) References Cited

U.S. PATENT DOCUMENTS 3,430,813 A * 3/1969 Gilmont ................ B01L 3/0282
                                                222/309
3,767,085 A   10/1973 Cannon et al.
(Continued)

OTHER PUBLICATIONS

"Seal." Merriam-Webster.com. Merriam-Webster, n.d. Web. Nov. 27, 2015.*

*Primary Examiner* — Robert Eom
(74) *Attorney, Agent, or Firm* — VLP Law Group LLP

(57) ABSTRACT

A mechanically-actuated vacuum-controlled fluid collection system includes a mechanically-actuated vacuum controller (MAVC) to draw fluid into a chamber through the opening to the chamber. The system may include a releasable seal to seal the opening, and the MAVC may include a spring-loaded plunger to create a vacuum within the chamber when sealed. The system includes multiple fluid chambers, and may further include a single actuator or multiple corresponding actuators. The system may be configured to add a pre-loadable reagent to fluid drawn into the one or more chambers, and may be configured to add the reagent in proportion to a volume of the fluid. The system may be controllable to release collected fluid to another device, such as for assay and/or transport. The system may be configured to draw a liquid biological sample such as urine, and may include a fluid interface to draw fluid from a biological sample container.

32 Claims, 10 Drawing Sheets

(51) Int. Cl.
*B01L 3/00* (2006.01)
*A61B 10/00* (2006.01)

(52) U.S. Cl.
CPC ............... *B01L 2300/0832* (2013.01); *B01L 2300/0864* (2013.01); *B01L 2400/0478* (2013.01)

(56) References Cited

U.S. PATENT DOCUMENTS

| | | | |
|---|---|---|---|
| 4,185,628 A | | 1/1980 | Kopfer |
| 4,690,005 A | * | 9/1987 | Tervamaki ............ B01L 3/0224 422/925 |
| 4,915,695 A | | 4/1990 | Koobs |
| 2011/0127294 A1 | * | 6/2011 | Pearcy ................. B01L 3/0272 422/501 |

* cited by examiner

MECHANICALLY ACTUATED VACUUM CONTROLLED FLUID COLLECTION

CROSS REFERENCE TO RELATED APPLICATIONS

This application claims the benefit of U.S. Provisional Patent Application No. 61/733,516, filed Dec. 5, 2012, which is incorporated herein by reference in its entirety.

BACKGROUND

Conventional fluid collection devices are not portable, mechanically actuated, and/or designed to collect a measured amount of liquid, interface with a liquid biological sample container, a transport device, and/or an assay device, and/or to add a pre-loaded reagent to collected fluid.

Figure 1A:
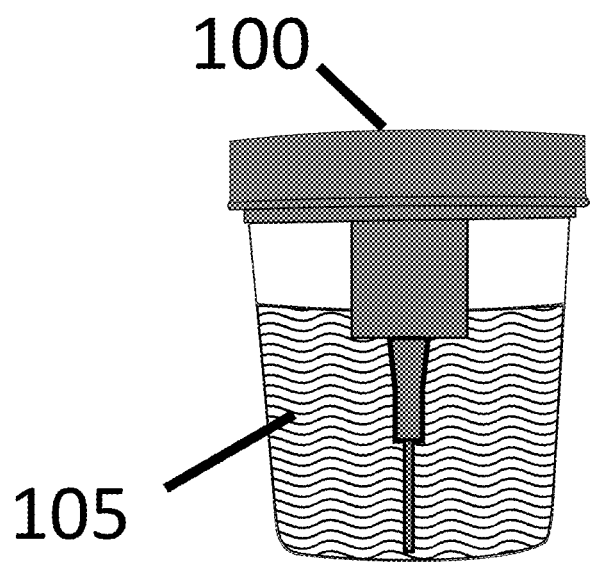
FIG. 1A illustrates a fluid collection device having a built-in sample collection interface to collect liquid or fluid.

In the drawings, the leftmost digit(s) of a reference number identifies the drawing in which the reference number first appears.

DETAILED DESCRIPTION

Disclosed herein are mechanically actuated vacuum fluid collection systems and methods.

FIG. 1A illustrates a fluid collection device 1000 having a built-in sample collection interface 100, to collect liquid or fluid 105. Fluid collection device 1000 may be configured and/or serve as a fluid collection device, such as to collect a biological fluid, such as urine, from a container or cup.

Figure 1B:
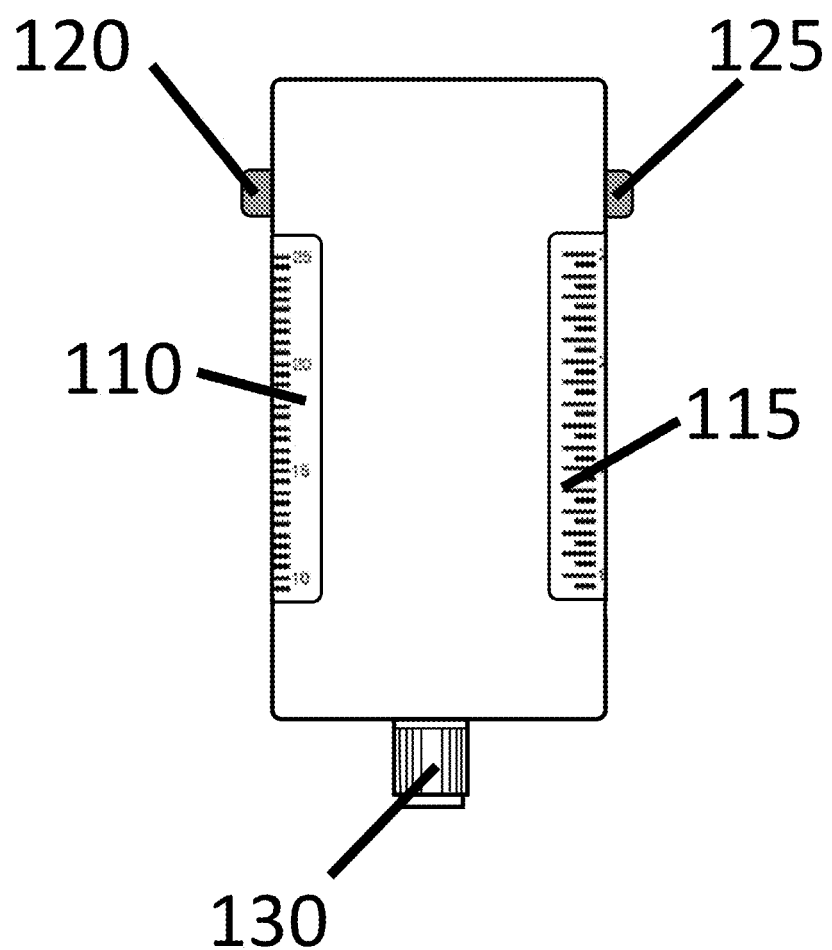
FIG. 1B is a front view of the fluid collection device of FIG. 1A.

FIG. 1B is a front view of fluid collection device 1000, including syringe units 110 and 115 and triggers 120 and 125 that are mechanically activated to initiate fluid collection by syringe units 110 and 115, respectively. A sample port 130 connects to sample collection interface 100 (FIG. 1A), to permit fluid communication between fluid sample 105 (FIG. 1A) and syringe units 120 and 125 when activated. Sample port 130 may include, without limitation, a straw, a pierceable membrane, a Luer lock, and/or or a one-way valve.

Figure 1C:
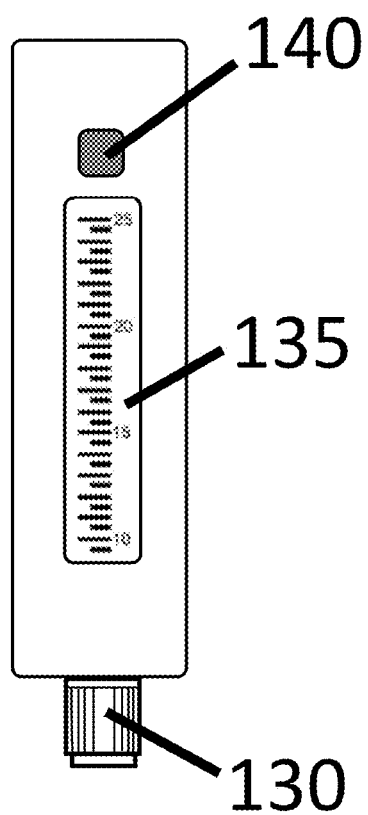
FIG. 1C is a side profile of the fluid collection device of FIG. 1A.

FIG. 1C is a side profile of fluid collection device 1000, including sample port 130, syringe unit 110, and corresponding trigger 120.

Fluid collection device 1000 may be configured as described with respect to one or more examples described below. Fluid collection device 1000 is not, however, limited to any of the examples below.

Figure 2:
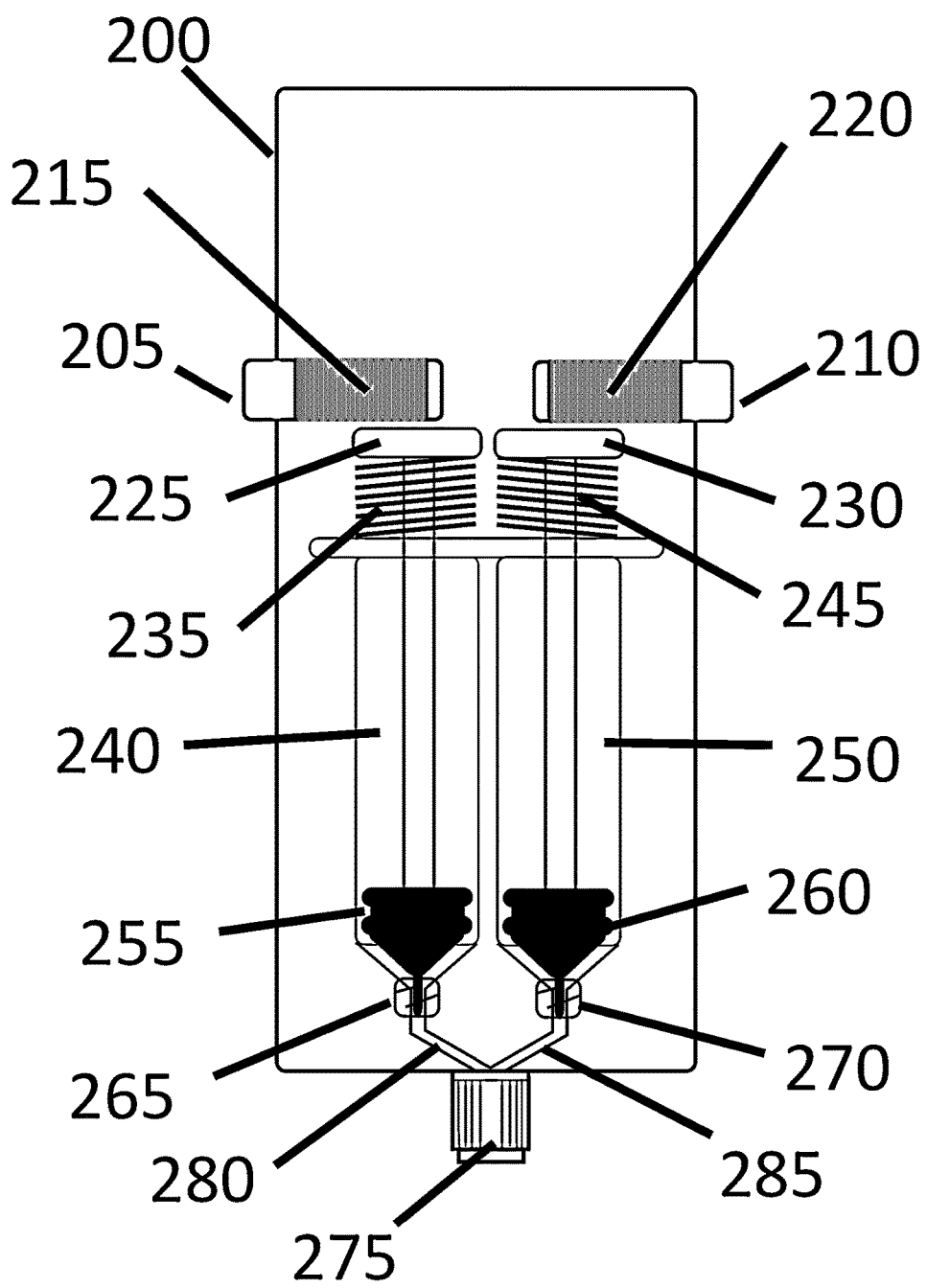
FIG. 2 is a cut-away front view of another fluid collection device.

FIG. 2 is a cut-away front view of a fluid collection device 2000, including an outer case 200, which may be removable. Outer case 200 may be shorter, relative to device 1000, than illustrated in FIG. 2.

Triggers 205 and 210 have openings 215 and 220 at their centers that, when corresponding triggers 205 and 210 are mechanically actuated, allow plungers 225 and 230 to rise, respectively.

Device 2000 may include springs spring 235 and 245 to provide a force for fluid collection. When trigger 205 is activated, spring 235 extends and pushes plunger 225 up through an opening 215 to create a vacuum to draw a fluid sample into a chamber, illustrated here as a syringe unit 240. When trigger 210 is activated, spring 245 extends and pushes plunger 230 up through opening 220 to create a vacuum to draw fluid into syringe unit 250. Triggers 205 and 210 may be actuated in tandem or in series.

Device 2000 may be configured to interface with a fluid collection container such as, for example, a urine collection container. Device 2000 may include stoppers 255 and 260 to form seals around inlets of syringe units 240 and 250, respectively.

Device 2000 may include adaptors 265 and 270 to connect syringe units 240 and 250 to sample port 275 via fluid channels 280 and 285, respectively. Adaptors 265 and 270 may include a Luer interface with fluid channels 280 and 285, respectively. Sample port 275 may include a rubber septum.

Fluid collection device 2000 may be configured as described with respect to one or more other examples described herein. Fluid collection device 2000 is not, however, limited to other examples herein.

Figure 3:
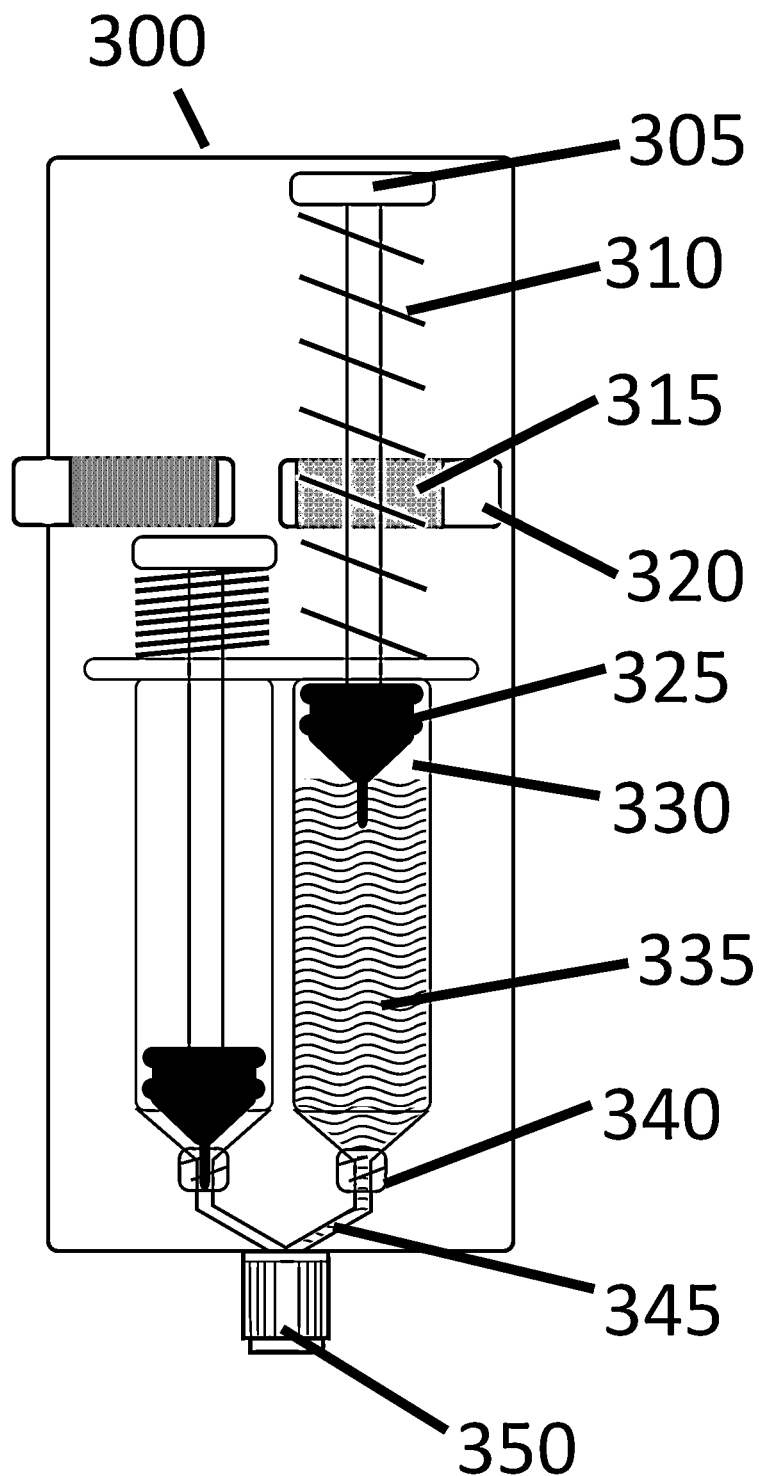
FIG. 3 is a cut-away front view of another fluid collection device after one of two syringe units has been activated.

FIG. 3 is a cut-away front view of a fluid collection device 3000 after one of two syringe units has been activated.

A plunger 305 has been extended by expansion of a spring 310 through an opening 315 following activation of a trigger 320. A stopper 325 has been drawn through syringe unit 330 and fluid sample 335 has been collected by suction.

An adaptor 340 connects a body of a syringe unit to a channel 345 that interfaces with a sample port 350, which is in fluid communication with a fluid sample.

Components of device 3000 may be contained within outer case 300.

Fluid collection device 3000 may be configured as described with respect to one or more other examples described herein. Fluid collection device 3000 is not, however, limited to other examples herein.

Figure 4:
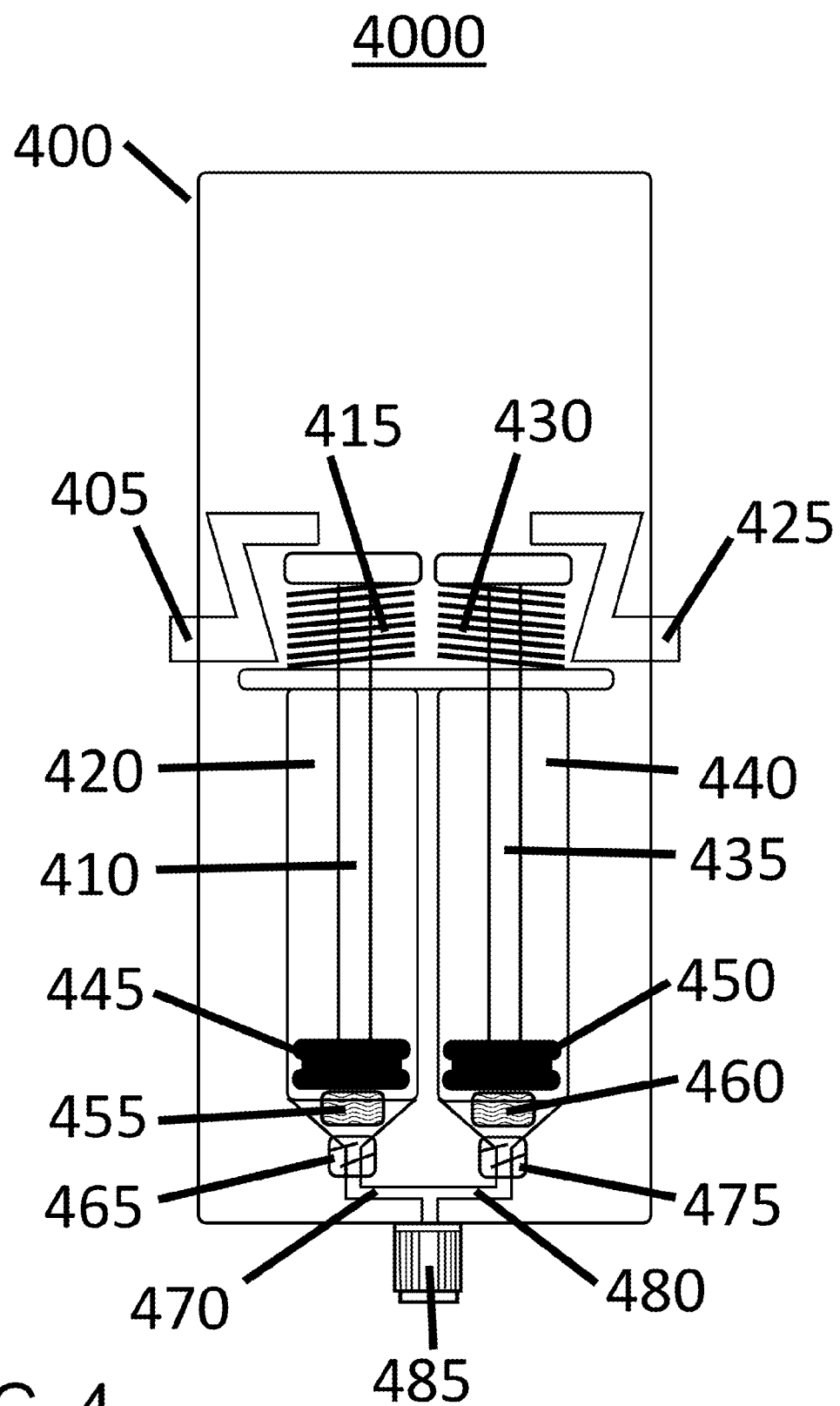
FIG. 4 is a cut-away front view of another fluid collection device that is preloaded with a reagent.

FIG. 4 is a cut-away front view of a fluid collection device 4000 that is preloaded with a reagent and includes a variation of an activation trigger. When activated, a trigger 405 releases a plunger 410 and a force from spring 415 causes it to extend and create a vacuum in a syringe unit 420. When a trigger 425 is activated, it allows a spring 430 to push up on a plunger 435, extending it and creating a vacuum in a syringe unit 440.

Syringe units 420 and 440 may be sealed with stoppers 445 and 450, respectively. In FIG. 4, syringe unit 420 contains a reagent 455, and syringe unit 440 contains reagent 460. As fluid is drawn into the syringe units, the fluid combines with reagents 455 and 460 to create a homogenous mixture. Syringe units 420 and 440 may be actuated in tandem or in series.

In an embodiment a volume of the fluid collected may be predetermined and/or measured.

In an embodiment a volume of the reagent may be predetermined and/or measured.

In FIG. 4, an adaptor 465 connects fluid channel 470 to syringe unit 420, and an adaptor 475 connects fluid channel 480 to syringe unit 440. Fluid channels 470 and 480 interface with sample port 485, which is in fluid communication with the fluid sample.

Components of device 4000 may be contained within outer case 400.

Fluid collection device 4000 may be configured as described with respect to one or more other examples described herein. Fluid collection device 4000 is not, however, limited to other examples herein.

Figure 5:
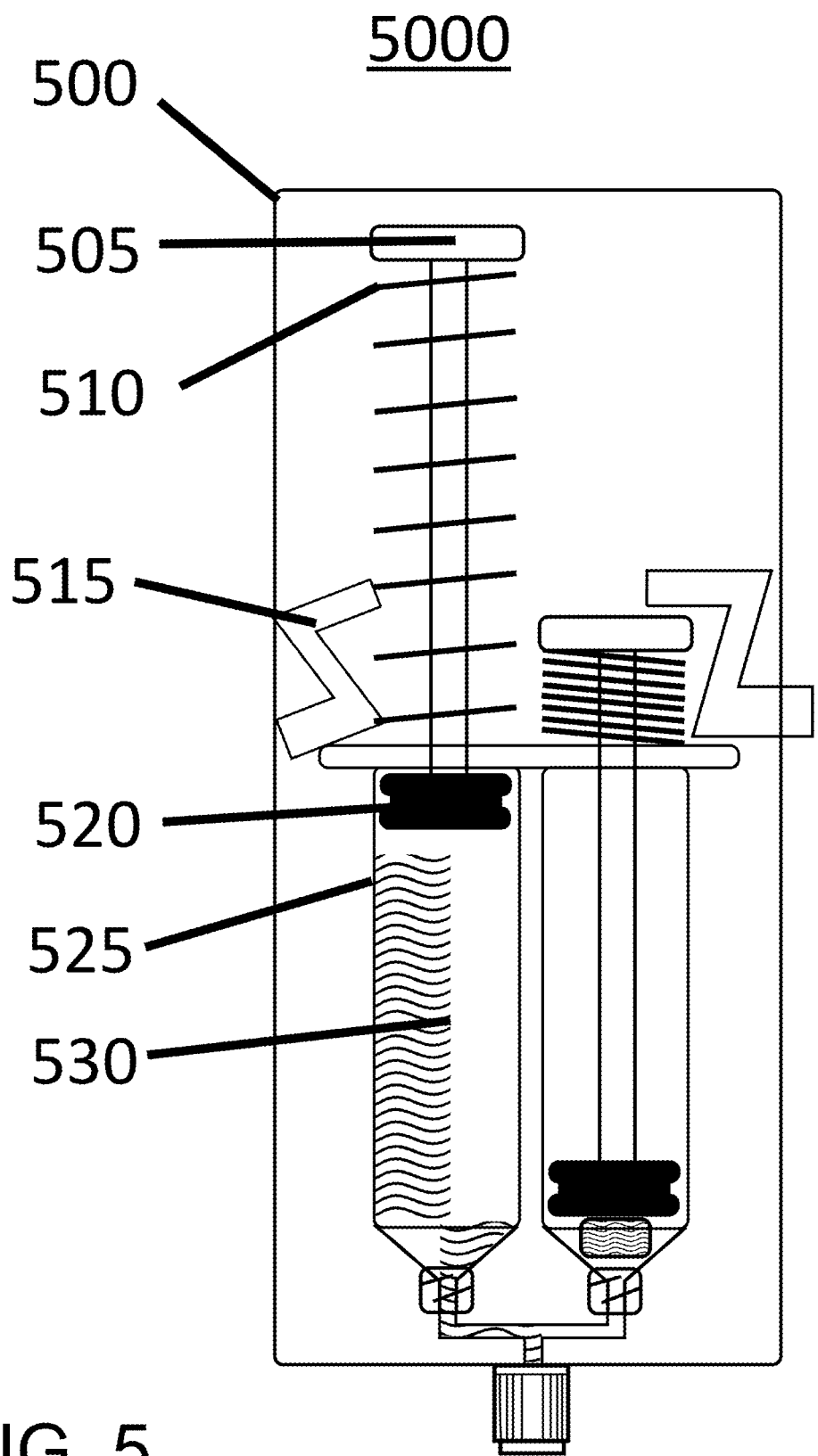
FIG. 5 is a cut-away front view of another fluid collection device that is preloaded with a reagent.

FIG. 5 is a cut-away front view of a fluid collection device 5000 that is preloaded with a reagent and includes a variation of a trigger after one syringe unit has been activated. A plunger 505 has been extended by a spring 510 following mechanical activation of a trigger 515. A stopper 520 has been drawn up through syringe unit 525, filling it with fluid sample 530. A preloaded reagent mixes with a fluid 530 as it is drawn into syringe unit 525, to provide a homogenous solution of sample and reagent.

Components of device 5000 may be contained within outer case 500.

Fluid collection device 5000 may be configured as described with respect to one or more other examples described herein. Fluid collection device 5000 is not, however, limited to other examples herein.

Figure 6A:
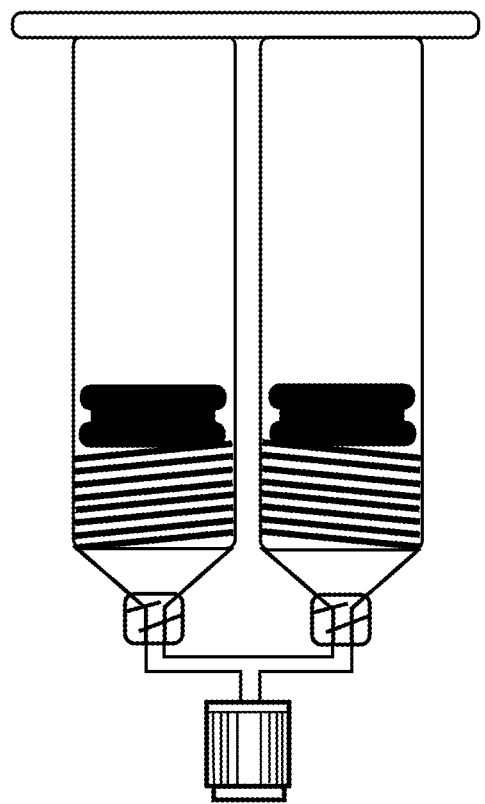
FIG. 6A is a cut-away front-view view of another fluid collection device having a two-stage plunger system and a preloaded reagent which may be added to a collected fluid in multiple installments.

FIG. 6A is a cut-away front-view view of a fluid collection device 6000, having a two-stage plunger system and a preloaded reagent which may be added in multiple installments. Fluid collection device 6000 may be configured as described below with reference to FIG. 6B and/or FIG. 6C.

Figure 6B:
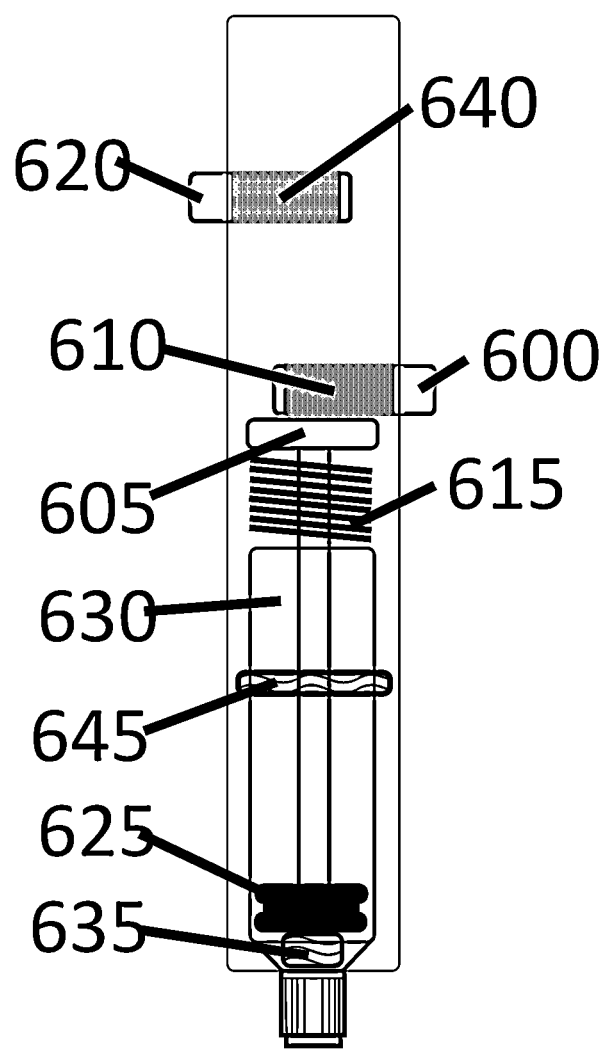
FIG. 6B is a cut-away side-view of an embodiment of the fluid collection device of FIG. 6A.

FIG. 6B is a cut-away side-view of an embodiment of fluid collection device 6000. When a trigger 600 is mechanically activated, it moves to allow a plunger 605 to pass through an opening 610 in trigger 600. A spring 615 extends plunger 605 until it comes into contact with a trigger 620, which has not yet been activated. A stopper 625 is drawn back by this action and a syringe unit 630 fills with a first portion of fluid sample. A reagent 635 mixes with the sample as is enters syringe unit 630. The amount of sample and/or reagent may be measured and/or predetermined.

Trigger 620, when pushed, activates a second stage of the plunge. It allows plunger 605 to pass through an opening 640 and further extend using force from a spring 615. As stopper 625 moves past a reagent deposit 645, an additional portion of fluid is drawn up and added to the previously-collected portion of sample.

Triggers 600 and 620 may be actuated sequentially, in that order, or trigger 600 only may be actuated.

Figure 6C:
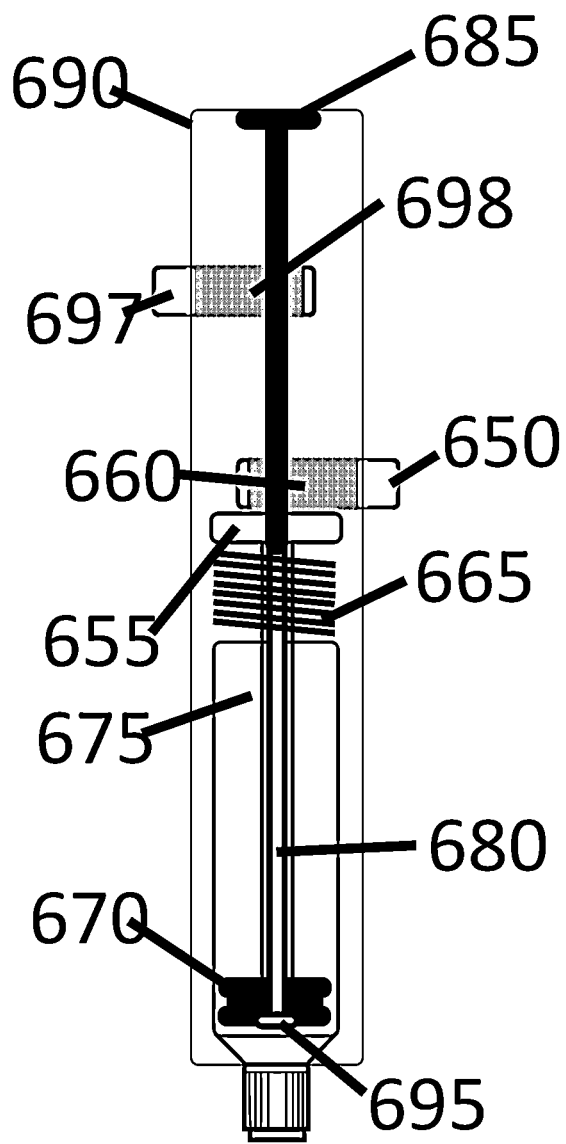
FIG. 6C is a cut-away side-view of another embodiment of the fluid collection device of FIG. 6A.

FIG. 6C a cut-away side-view of another embodiment of fluid collection device 6000, having a preloaded reagent that is added proportionally to the fluid sample being collected.

When a trigger 650 is actuated, a plunger 655 extends through an opening 660 by force of a spring 665. This draws back a stopper 670 and fills a syringe unit 675 with fluid sample. A reagent 680 is forced out of a hollowed plunger 655 as it moves upward into a solid plunger 685, which is fixed to an outer device case 690. As this happens, a one-way valve 695 adds reagent 680 proportionally to the fluid sample to provide a mixed solution. Valve 695 may include a stopper.

A trigger 697 activates a second stage of the plunge and collection of an additional portion of fluid sample by allowing plunger 655 to pass through an opening 698 by the force of spring 665. Upward movement of hollowed plunger 655 moves it upward onto solid plunger 685, which pushes reagent 680 out of one-way valve 695. Reagent 680 is forcibly mixed with the fluid sample to provide a homogenous mixture.

Triggers 650 and 697 may be activated sequentially, in that order, or trigger 650 alone may be activated.

A device as disclosed herein may be configured to collect a liquid or fluid that includes a biological sample such as, without limitation, a urine sample.

A device as disclosed herein may include a push-button to actuate a trigger.

A device as disclosed herein may include retractable plunger to create a vacuum in the device in order to collect a fluid.

A device as disclosed herein may include a spring configured to provide sufficient for to fill the device.

A device as disclosed herein may be configured to draw up portions of fluid in sequence and/or in parallel, and may be configured to accommodate one or more of a variety of volumes, which may include a measured volume and/or a predetermined volume.

A device as disclosed herein may include one or more sealable chambers for collection of fluid samples. The device may be configured, for example, to seal the samples for transport. A sealable chamber(s) may have more than one stop, with each stop collecting a portion of fluid. A sealable chamber may include a syringe.

In some embodiments, reagent may be added to these portions. The sample and reagent may be forcibly mixed in the sample collection chamber. In some embodiments the addition of reagent may be proportional to the amount of fluid collected.

A device as disclosed herein may be preloaded with a liquid reagent.

A device as disclosed herein may be preloaded with a dry reagent.

A device as disclosed herein may be configured to release and/or expel collected fluid, such as for assay and/or transport.

A device as disclosed herein may be configured to release and/or expel a portion of collected fluid.

A device as disclosed herein may be configured to release and/or expel a measured and/or adjustable amount of collected fluid.

A device as disclosed herein may include an openable external case to provide access to collected fluid.

A device as disclosed herein may be configured to release collected fluid by pushing a plunger.

A device as disclosed herein may include membrane or rubber septum, which may be punctured to release or expel collected fluid.

A device as disclosed herein may include a fluid interface to transfer collected fluid to a diagnostic or transport system.

A device as disclosed herein may include a fluid interface to draw fluid from a urine collection cup.

Methods and systems are disclosed herein with the aid of functional building blocks illustrating functions, features, and relationships thereof. At least some of the boundaries of these functional building blocks have been arbitrarily defined herein for the convenience of the description. Alternate boundaries may be defined so long as the specified functions and relationships thereof are appropriately performed. While various embodiments are disclosed herein, it should be understood that they are presented as examples.

The scope of the claims should not be limited by any of the example embodiments disclosed herein.

What is claimed is:

1. A fluid collection device, comprising:
   a housing having a fluid chamber configured to receive, mix, and retain a fluid and a reagent, and an opening to the fluid chamber;
   a mechanically-actuated vacuum controller to draw a fixed, predetermined amount of the fluid into the fluid chamber through the opening;
   the housing further including a reagent chamber, the reagent chamber disposed in-line behind the opening, with a fixed, predetermined amount of a reagent predisposed in the reagent chamber prior to activation of the mechanically-actuated vacuum controller;
   the mechanically-activated vacuum controller is further configured to draw in a fixed, measured volume of fluid through the opening, to thereby mix the reagent with the measured volume of fluid in a predetermined proportion in the fluid chamber, as the fixed, measured volume of fluid is drawn sequentially through the opening, through the reagent chamber, and then into the fluid chamber by the mechanically-actuated vacuum controller; and
   the fluid chamber configured to store the mixed fluid and reagent for transport within the device.

2. The device of claim 1, wherein
   the reagent chamber is configured to hold a fixed, predetermined amount of liquid reagent.

3. The device of claim 1, wherein:
   the fluid chamber includes first and second fluid chambers and the opening includes first and second openings to the respective first and second fluid chambers; and
   the mechanically-actuated vacuum controller is configured to draw fluid into the first and second fluid chambers through the respective first and second openings.

4. The device of claim 1, wherein the housing further has an outlet to expel the mixed fluid and reagent from the fluid chamber.

5. The device of claim 4, wherein the mechanically actuated vacuum controller is configured to expel the mixed fluid and reagent from the fluid chamber through the outlet.

6. The device of claim 1, wherein the mechanically-actuated vacuum controller is configured to draw a biological sample fluid into the fluid chamber through the opening.

7. The device of claim 1, further including a push-button based actuator to actuate the mechanically-actuated vacuum controller.

8. The device of claim 1, further including a fluid stopper, disposed within or on the housing, to releasably seal the opening to the fluid chamber for transport of the mixed fluid and reagent.

9. The device of claim 8, wherein the mechanically-actuated vacuum controller includes a retractable plunger to create a vacuum within the fluid chamber when the fluid stopper is engaged to seal the opening.

10. The device of claim 9, wherein the mechanically-actuated vacuum controller includes a spring to apply a mechanical force to the retractable plunger.

11. The device of claim 1, further including a push button to trigger the mechanically-actuated vacuum controller to draw fluid into the fluid chamber through the opening.

12. The device of claim 1, wherein the mechanically-actuated vacuum controller includes a retractable plunger to create a vacuum in the first chamber to draw the fluid into the first chamber through the opening.

13. The device of claim 1, wherein the mechanically-actuated vacuum controller includes a spring to provide a force to draw the fluid sequentially through the opening, through the reagent chamber, and then into the fluid chamber.

14. The device of claim 1, wherein the mechanically-actuated vacuum controller is configured to draw in and retain multiple fixed, metered volumes of fluid into the fluid chamber sequentially or in parallel.

15. The device of claim 14, wherein the mechanically-actuated vacuum controller is further configured to draw in and retain multiple portions of the fixed, metered volumes of fluid.

16. The device of claim 1, wherein the fluid chamber has multiple sealable fluid chambers to receive a collection of mixed fluid and reagent samples.

17. The device of claim 16, further including seals, disposed within the housing, to seal the sealable fluid chambers.

18. The device of claim 16, wherein at least one of the sealable chambers has multiple stops to collect multiple corresponding portions of mixed fluid and reagent.

19. The device of claim 16, wherein the at least one of the sealable chambers includes a respective syringe housing.

20. The device of claim 1, wherein the fluid chamber and the mechanically-actuated vacuum controller are configured to mix each of multiple measured portions of fluid drawn into the fluid chamber with the reagent, within the fluid chamber.

21. The device of claim 20, wherein the fluid chamber and the mechanically-actuated vacuum controller are further configured to forcibly mix the multiple portions of measured fluid with the reagent, within the fluid chamber.

22. The device of claim 20, wherein the mechanically-actuated vacuum controller is configured to add reagent in proportion to volumes of the respective multiple portions of measured fluid.

23. The device of claim 1, wherein the reagent chamber is preloaded with a liquid reagent.

24. The device of claim 1, wherein the reagent chamber is preloaded with a dry reagent.

25. The device of claim 1, wherein the fluid chamber is further configured to be emptied of the stored, mixed fluid and reagent following transport of the device.

26. The device of claim 25, wherein the mechanically-actuated vacuum controller is configured to dispense multiple portions of the stored, mixed fluid and reagent from the fluid chamber following transport of the device.

27. The device of claim 26, wherein the mechanically-actuated vacuum controller is further configured to dispense multiple measured portions of the stored, mixed fluid and reagent.

28. The device of claim 1, wherein the mixed fluid and reagent stored within the fluid chamber is accessible by opening the housing.

29. The device of claim 1, wherein the mixed fluid and reagent stored within the fluid chamber is releasable by pushing a plunger.

30. The device of claim 1, further including one or more of a pierce-able membrane and rubber septum disposed over the opening.

31. The device of claim 1, configured to interface with a diagnostic or transport system.

32. The device of claim 1, further including:
   a mechanical actuator to actuate the mechanically-actuated vacuum controller, wherein a portion of the mechanical actuator extends through a surface of the housing to permit a user to actuate the mechanically-actuated vacuum controller: and wherein the reagent and the mechanically-actuated vacuum controller are pre-disposed within the housing, inaccessible to a user of the device.

* * * * *